United States Patent
Pretzlaff et al.

(10) Patent No.: US 8,674,239 B2
(45) Date of Patent: Mar. 18, 2014

(54) FEEDTHROUGH CONDUCTOR FOR ELECTRONIC COMPONENTS

(75) Inventors: Bernd Pretzlaff, Mildstedt (DE); Holger Lippitz, Berlin (DE)

(73) Assignee: LITRONIK Entwicklungs GmbH, Husum (DE)

( * ) Notice: Subject to any disclaimer, the term of this patent is extended or adjusted under 35 U.S.C. 154(b) by 135 days.

(21) Appl. No.: 13/363,553

(22) Filed: Feb. 1, 2012

(65) Prior Publication Data

US 2012/0205150 A1  Aug. 16, 2012

Related U.S. Application Data

(60) Provisional application No. 61/441,287, filed on Feb. 10, 2011.

(51) Int. Cl.
*H02G 3/02* (2006.01)
*H01B 17/26* (2006.01)

(52) U.S. Cl.
USPC ............... 174/650; 174/152 GM; 174/50.61; 361/302

(58) Field of Classification Search
USPC ...... 174/650, 152 G, 520, 50.5, 50.52, 50.51, 174/50.61; 429/181; 361/302, 307, 306.1, 361/320; 333/182
See application file for complete search history.

(56) References Cited

U.S. PATENT DOCUMENTS

| | | | |
|---|---|---|---|
| 3,354,359 A | 11/1967 | Ford | |
| 4,296,458 A | 10/1981 | Smith et al. | |
| 4,424,551 A * | 1/1984 | Stevenson et al. | 361/302 |
| 6,812,404 B1 * | 11/2004 | Martinez | 174/50.61 |
| 7,064,270 B2 * | 6/2006 | Marshall et al. | 174/152 GM |
| 7,365,960 B2 | 4/2008 | O'Phelan et al. | |
| 7,535,693 B2 * | 5/2009 | Stevenson et al. | 361/302 |
| 7,539,004 B2 * | 5/2009 | Iyer et al. | 361/302 |
| 7,696,002 B1 | 4/2010 | Ribble et al. | |
| 7,837,085 B1 | 11/2010 | Tziviskos | |

(Continued)

FOREIGN PATENT DOCUMENTS

| | | |
|---|---|---|
| DE | 1 564 766 | 3/1970 |
| DE | 26 45 323 | 4/1978 |

(Continued)

OTHER PUBLICATIONS

European Search Report and Notes to the European Search Report on European Patent Application No. EP 12 15 1781, dated May 31, 2012 (7 pages).

(Continued)

*Primary Examiner* — Angel R Estrada
(74) *Attorney, Agent, or Firm* — Buchanan Ingersoll & Rooney PC

(57) ABSTRACT

The present disclosure relates to feedthrough contacts for electronic components of the type used in implantable stimulators such as, for example, cardiac pacemakers, ICDs, CRT-Ds, and/or neurostimulators. A feedthrough conductor includes a metallic electrode, wherein a part of the metallic electrode (2) has a locally enlarged diameter in the region of the passage through an opening (3) in the component housing (4). The ridge (5) formed as a result exerts pressure onto the elastic sealing material (6) disposed around the electrode (2) in a tubular shape, thereby producing a hermetic seal between the electrode surface and the sealing material (6), and between the sealing material (6) and the wall (4) of the housing opening (3). The feedthrough conductor is sealed using an adhesive material (7) on the outer side of the electronic component.

18 Claims, 4 Drawing Sheets

(56) References Cited

U.S. PATENT DOCUMENTS

| | | |
|---|---|---|
| 2008/0043403 A1 | 2/2008 | Ueda et al. |
| 2008/0154320 A1 | 6/2008 | Sherwood |
| 2008/0190647 A1 | 8/2008 | Itoh |
| 2008/0259528 A1 | 10/2008 | Fujita et al. |

FOREIGN PATENT DOCUMENTS

| | | |
|---|---|---|
| EP | 0 083 271 | 7/1983 |
| WO | 0243090 | 5/2002 |
| WO | 2010028433 | 3/2010 |

OTHER PUBLICATIONS

European Search Report and Notes to the European Search Report on European Patent Application No. EP 12 15 1781, dated Dec. 19, 2012 (11 pages).

\* cited by examiner

FEEDTHROUGH CONDUCTOR FOR ELECTRONIC COMPONENTS

CROSS-REFERENCE TO RELATED APPLICATIONS

This patent application claims the benefit of U.S. Provisional Patent Application No. 61/441,287, filed on Feb. 10, 2011, which is hereby incorporated by reference in its entirety.

TECHNICAL FIELD

The present disclosure relates to electrical feedthrough holes and, in particular, electrical feedthrough holes for components in electrical implants used in the human body.

BACKGROUND

Electronic implants have been used in modern medical technology as microstimulators having diverse embodiments, and are used, for example, as cardiac pacemakers, defibrillators (ICDs, CRT-Ds, etc.) and/or neurostimulators.

Such implants generally have a number of electrical contacts which are used to receive and transmit electrical pulses measured by probes, and electrode leads are provided that transmit stimulating signals from a control unit to one or more implanted electrodes for stimulation. For example, a cardiac pacemaker can detect the excitation pulses of the heartbeat generated by the sinoatrial node and output stimulating electrical signals to one or more stimulating electrodes on the heart if aberrations are present, e.g., in the pulse rate.

Such an implantable arrangement for stimulation is described in U.S. Publication No. 2008/0154320, for example. The cardiac pacemaker described in that publication is comprised of a housing, in which a battery and the biometric evaluation and control electronics and, in particular, a capacitor are accommodated, the capacitor being used to generate and transmit electrical stimulating pulses to at least one electrode lead extending out of the housing.

The requirements on the quality of the transmitted signals is very high, of course, in particular for excitation pulses that act directly on central functions of human organs. This applies for the precise, time-based output of an excitation pulse or a sequence of pulses, and for the regulation and stabilization of the suitable pulse shape and electrical intensity.

The properties of the capacitor integrated in the implant determine, to a non-insubstantial extent, the intensity and quality of the transmitted signal shape that can be achieved. U.S. Publication No. 2008/0154320 therefore proposes the use of special oxides to form a separating layer between the anode and the cathode of the capacitor, which has high dielectric constants and, therefore, provides the greatest possible capacitance combined with the smallest possible capacitor volume.

Implanted stimulators can now remain in the human body for years in some cases. A requirement therefore is that the housing and the electrode leads of such an implant be comprised of a material that has the highest possible biocompatibility, thereby ensuring that no substances are released into the body that could cause metabolic harm.

Every implant that is installed in the human or other body is surrounded for the entire operating period by a physical medium, namely, a mixture of various chemical components that is relatively reactive due to the different dissolved ions in particular. A permanent hermetic seal of the implant housing must therefore fulfill special requirements. The purpose thereof is to prevent bodily fluid from entering the implant and thereby ensure that all internal electronic components are protected, and to prevent substances (battery media, capacitor electrolytes, etc.) that are present in the interior of the implant and could harm the organism from escaping and entering the physical medium.

The seal in the region of a feedthrough hole of an electrode through an opening in the housing wall of the implant is particular problematic in that particular case. To ensure that the external physical medium and, e.g., electrolyte present inside the capacitor are reliably separated in this region, the seal must be comprised of a non-ageing material which has appropriate mechanical properties for a seal and is stable against the chemical effects of bodily fluid and the substances that may be adjacent thereto on the internal side.

High requirements are also placed on the feedthrough holes in the electronic components used in the implant, in particular, in batteries and/or capacitors. For example, the electrical feedthrough holes in a capacitor must function as a barrier to the electrolytes that cannot be overcome, at least for the duration of the expected service life of the implant, in order to protect the interior of the implant against leaking electrolyte solution, and to safeguard the functionality of the capacitor and, therefore, the implant.

To this end, the metallic electrode in the feedthrough hole is typically enclosed by elastic sealing material in the region of the passage. Elastomer-based plastics are suitable, for instance, and, in the case of an electrically conductive housing material, the sealing material simultaneously functions as electrical insulation. In the process of fabricating a permanent hermetic seal of the electrode feedthrough hole, all surface patches that abut one another, i.e., between the electrode and the sealing material, and between the sealing material and the housing wall, must therefore be joined to one another in a manner free of joints and pores.

U.S. Pat. No. 7,365,960 relates to this technical field. It describes an electrode feedthrough hole of a capacitor for implants that is sealed using a specially formed sealing flange.

FIGS. 1A and 1B (prior art) show a cross section of the electrode feedthrough hole and the sealing flange inserted therein, according to U.S. Pat. No. 7,365,960. FIGS. 1A and 1B are reproductions of FIGS. 11 and 12 of the '960 patent and, accordingly, the same reference numbers as used in the '960 patent are provided thereon. However, only a general description of these figures will be provided herein. In general, the sealing flange, which is comprised of rubber or elastic plastic, has an inner feedthrough hole through which a conductive connecting piece of the capacitor disposed in the implant extends. The connecting piece is designed as a hollow cylinder into which the further-extending electrode lead is inserted centrally from the outside. Since the feedthrough hole of the sealing flange has a cross section that is smaller than the electrode diameter (see FIG. 1B), pressure is generated when the arrangement is assembled, thereby ensuring that a seal exists between the electrode and the flange. To form the seal against the housing, the flange comprises an outer, annularly circumferential groove, into which the housing wall engages after the flange has been inserted. The dimensions of the groove are also intended to be slightly smaller than the thickness of the housing wall, and therefore the elastic sealing material rests tightly against the housing wall on both sides after the flange has been inserted into the housing opening.

The arrangement provided for the feedthrough of a capacitor contact for implants has the disadvantage that production is relatively costly due to the special shaping of the sealing flange since the circumferential groove of the flange must fit precisely into the housing opening when the arrangement is assembled. In addition, the electrical feedthrough using a plug connection between the further-extending, outer electrode lead and the metallic connecting piece to the capacitor requires that these transition pieces be produced with the most exact fit possible and be joined accordingly.

The present disclosure is directed to a feedthrough conductor for implants as, for example, disclosed in U.S. Pat. No. 7,365,960, as the closest prior art. The problem to be solved is that of developing a feedthrough conductor for electronic components, such as those used in permanently implantable stimulators, which meets the requirements for sealing and has additional advantages, thereby ensuring that the electrode, sealing material, and housing may be easily joined. A further problem to be solved by the disclosure is that of providing such a feedthrough conductor for capacitors, in the case of which the electrode surface of the capacitor contact can also be shaped and anodized up to a defined region of the feedthrough hole.

The present inventive disclosure is further directed toward overcoming one or more of the above-identified problems.

SUMMARY

One or more problems are solved in the case of a feedthrough conductor for electronic components, e.g., permanently implantable stimulators, having the features of the independent claim(s). Further features of advantageous embodiments of the disclosure are the subject matter of the dependent claims.

According to the disclosure, a metallic electrode has a locally enlarged diameter in the region of the passage through an opening in the component housing, which is designed such that an elastic sealing material disposed around the electrode in a tubular shape is widened in this region. The elastic sealing material therefore bears closely against the electrode in this widened region under pressure, thereby producing a reliable seal between the electrode surface and the sealing material. By way of the widened region, the tubular sealing material is also pressed against the wall of the opening in the component housing, thereby producing the necessary seal against the housing wall in this region. To affix the electrode in this position, a strongly adhesive material is applied on the side of the feedthrough hole leading away from the components, such as, for example, glue, synthetic resin, or the like, which encloses the electrode and completely covers the opening in the component housing. It is therefore ensured that the electrode and the sealing material are affixed in the desired position, and that the electrode feedthrough hole is provided with an additional seal against the exterior.

Various other objects, aspects and advantages of the present inventive disclosure can be obtained from a study of the specification, the drawings, and the appended claims.

The feedthrough conductor will be described in greater detail in the following using preferred embodiments, with reference to the drawings and the reference characters noted therein.

DETAILED DESCRIPTION

Figure 1A:
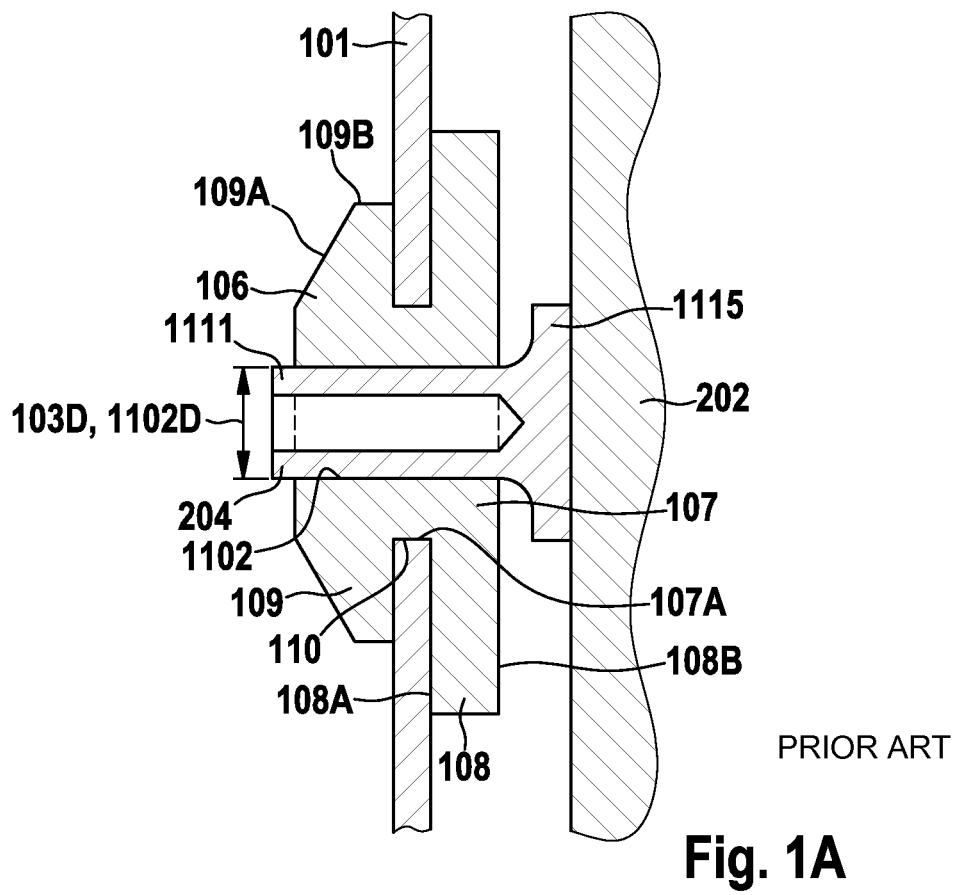
FIGS. 1A and 1B show the prior art, feedthrough conductor according to U.S. Pat. No. 7,365,960.
Figure 1B:
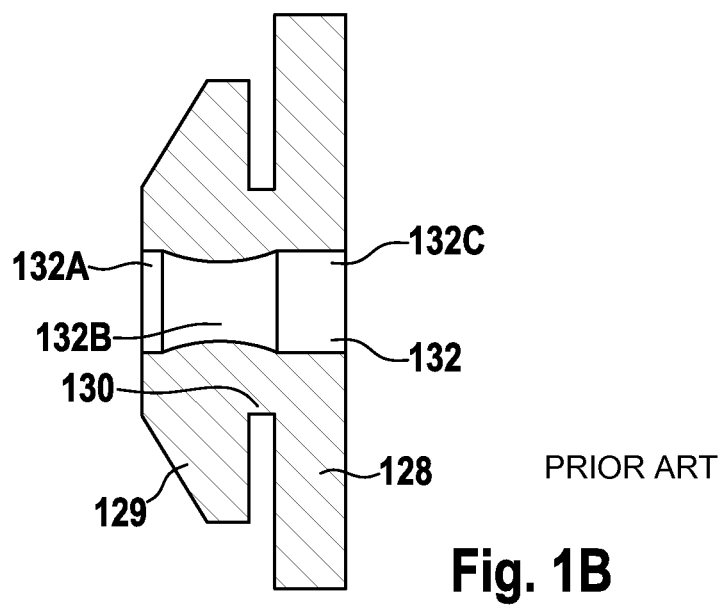
Figure 2:
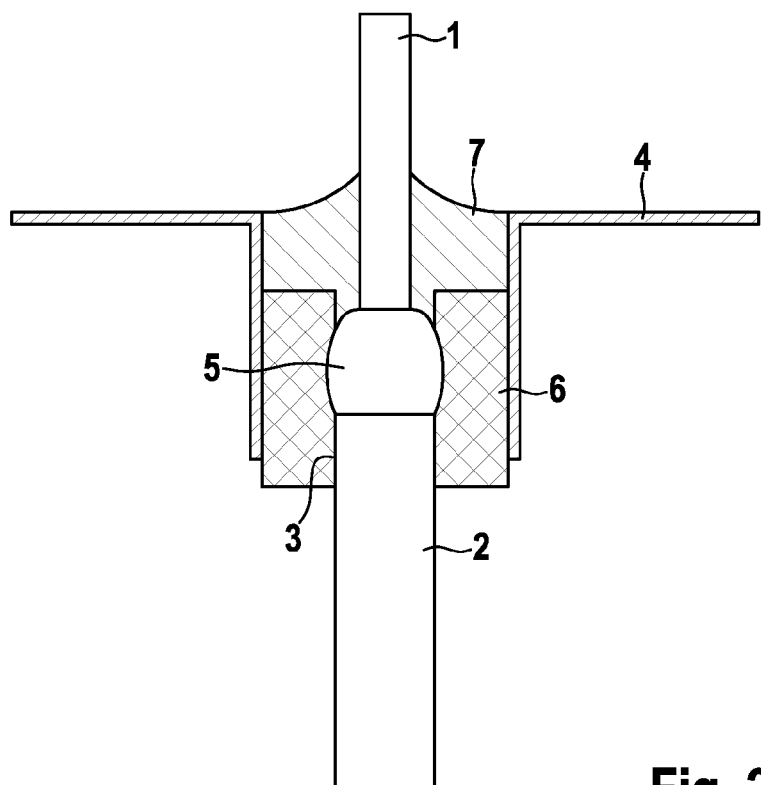
FIG. 2 shows a cross section through a first embodiment of the feedthrough conductor according to the disclosure.

FIG. 2 shows a first embodiment of the feedthrough conductor according to the disclosure, as a sectional image. In this example, the feedthrough conductor is comprised of two sections: an outer section 1 extending from a component, such as, for example, a capacitor or a battery, and an inner section 2. The cross section of electrode 2 is widened locally in the region of opening 3 in wall 4 of the component. In this embodiment, the widened region is shaped as a round profile. Ridge 5 is formed, as a result, and exerts pressure onto elastic sealing material 6 disposed around electrode 2 in a tubular shape, thereby producing a sealing effect between the electrode surface and the sealing material, and between the sealing material and the wall of housing opening 3. On the outer side of the component, the feedthrough conductor is sealed using an adhesive material 7, such as, for example, epoxide resin. Preferably, this material can also be used to mechanically affix electrode 1 in the position shown, thereby stabilizing the feedthrough conductor against any pushing or pulling forces by outer electrode 1.

In the production of the electrode assembly, it is essential that electrode 2 be positioned correctly together with tubular sealing material 6 inside opening 3. In terms of production engineering, it is advantageous for opening 3 to have a slightly larger local cross section, preferably in the central region of the passage (not shown in FIG. 2). Once electrode section 2 has been installed, it engages in this region of the opening in a form-fit manner by way of sealing material 6 which is expanded in the region of ridge-like thickened region 5. In this manner, electrode 2 in combination with sealing tube 6 slid thereon can be easily inserted into opening 3 until ridge-shaped expansion 5 becomes seated with an exact fit. The sizing of the cross section of opening 3, which is slightly enlarged locally, is also dependent on the material thickness of the tubular sealing material and is preferably selected such that the desired pressure between sealing material 6 and the wall of the opening is ensured in the installed state.

In the schematic depiction in FIG. 2, tubular sealing material 6 terminates in front of the outer edge of opening 3, directly behind ridge-shaped expansion 5. In this case, adhesive material 7 can also partially fill opening 3 from the outside. This arrangement is particularly advantageous when the electrode is comprised of different sections, as shown in FIG. 2. However, in the case of a simple electrode lead having a single cross section, sealing material 6 can be extended outwardly by way of ridge 5, and also the seal opening 3 up to the passage to the outside.

The feedthrough conductor according to the disclosure can be embodied in a particularly advantageous manner when the electrode, or the electrode sections, and opening 3 have a cylindrical geometry. In this case of circular cross sections, the pressure conditions between the electrode surface, sealing material, and housing wall are distributed with radial symmetry. This necessarily correlates with a centering of the electrode within the opening, thereby also optimizing the electrical insulation values relative to the housing wall of the electronic components.

The segmenting of the electrode depicted in FIG. 2 is particularly advantageous for the feedthrough of a capacitor contact since each electrode section 1, 2 can be tailor-made for the different requirements in the interior space and exterior space of the electronic components. This does not apply only for the dimensions depicted schematically in the figure as a change in cross section, but also primarily for the selection of the material. For capacitor contacts it has proven advantageous for the electrode inside a capacitor space to have contact with the electrolyte located therein. As a result, the surface of the electrode (=anode) can be oxidized in this region, as the desired electrochemical process, provided a suitable material selection is present. This process is also referred to as forming the electrode, or anodizing. If the electrode is comprised of aluminum or an aluminum-containing alloy, for example, an aluminum oxide layer forms on the surface. It has been shown that the occurrence of unwanted lost currents due to reforming processes, among other things, can be reduced as a result.

To make such forming possible, in one embodiment of the feedthrough conductor according to the disclosure, the surface of electrode section 2 extending to the capacitor can be structured such that an electrolyte present on the inner side of the electronic component can also reach the electrode surface in the region of sealing material 6. The structuring can take on different forms and is preferably limited to a defined subregion of electrode section 2.

Figure 3:
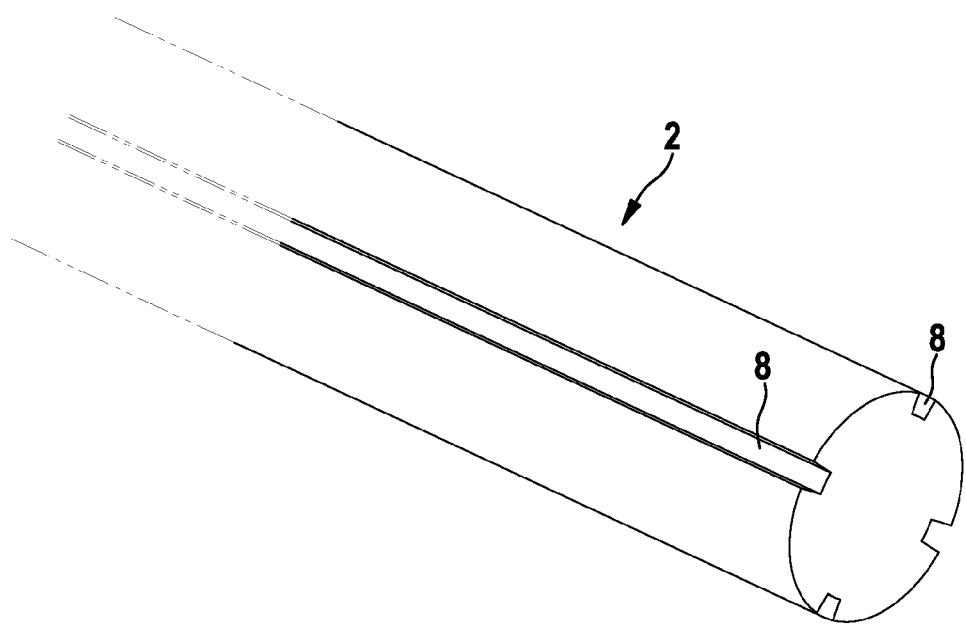
FIG. 3 shows an embodiment of a channeled structuring of the surface of an electrode section, according to the disclosure, for anodizing.

FIG. 3 shows a schematic view of a first embodiment of a structuring of the electrode surface in the region of electrode section 2. For this purpose, the electrode has recesses 8 in this region, which are formed in the surface and extend linearly. In the assembled state of the feedthrough conductor, liquid electrolyte from the region of the capacitor disposed in the interior of the component housing can travel along these groove-shaped structures and into the region between sealing material 6 and the electrode surface and thereby trigger anodization. The profile, depth, number, and geometric course of recesses 8 can be varied within wide limits, thereby making it possible to provide the particular conditions, e.g., the necessary material quantity of electrolyte, for the forming process.

Figure 4:
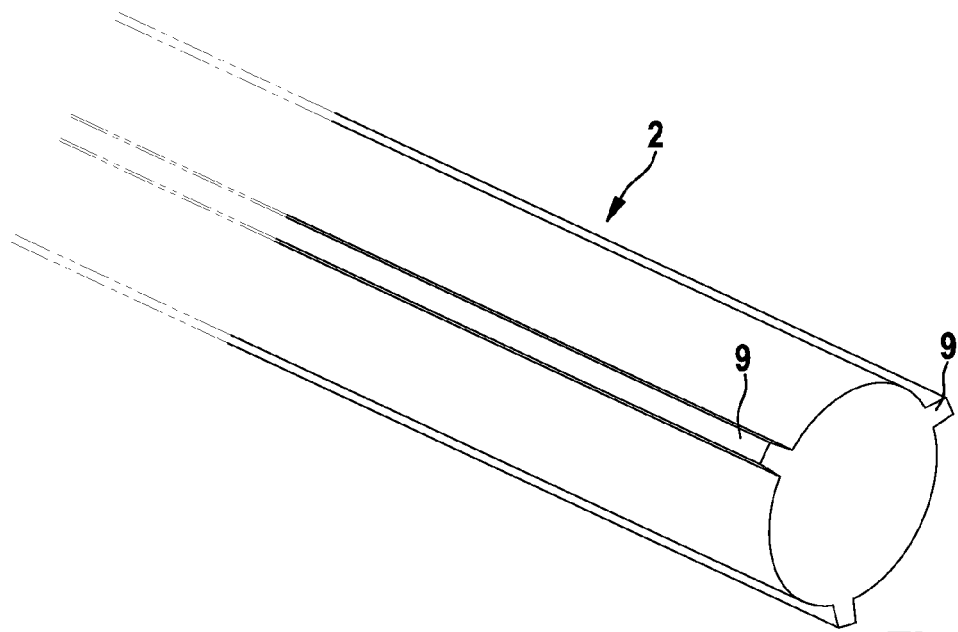
FIG. 4 shows an embodiment of a land-shaped structuring of the surface of an electrode section, according to the disclosure.

As shown in FIG. 4, instead of recesses in the electrode surface, it is possible for lands 9, or another type of raised embossing or protrusion, to be present as the structuring. Small intermediate spaces shaped as channels, for instance, are also created along such raised areas underneath sealing material 6, which are used as paths for the diffusion of electrolyte.

Figure 5:
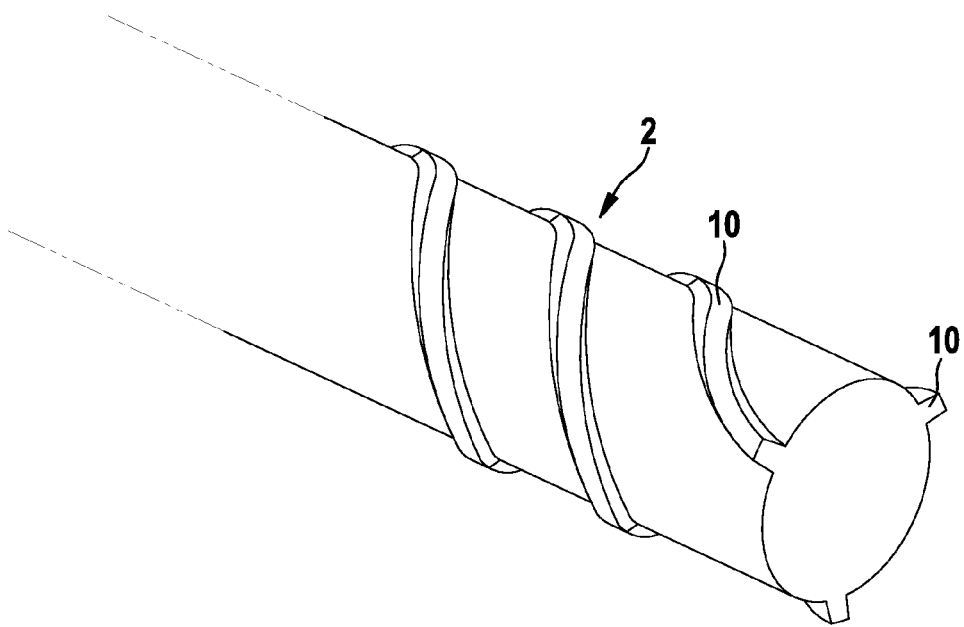
FIG. 5 shows an embodiment of an alternative geometric design of a structuring of the surface of an electrode section, according to the disclosure.

In FIGS. 3 and 4, structurings 8 and 9 are depicted as extending linearly parallel to the electrode axis. However, other geometric designs are also possible and are contemplated herein. A land 10 that extends in a spiral shape is shown in FIG. 5 as an example. In addition, it is not absolutely necessary for structures 8, 9, and/or 10 to be continuously linear. For example, a relief-type distribution of individual raised areas (land sections, nubs, protrusions, etc.) or recesses (cutouts, grooves, channels, etc.) also results in the formation of residual intermediate spaces, by way of which the electrolyte can advance toward the electrode surface by way of the capillary effect.

Figure 6:
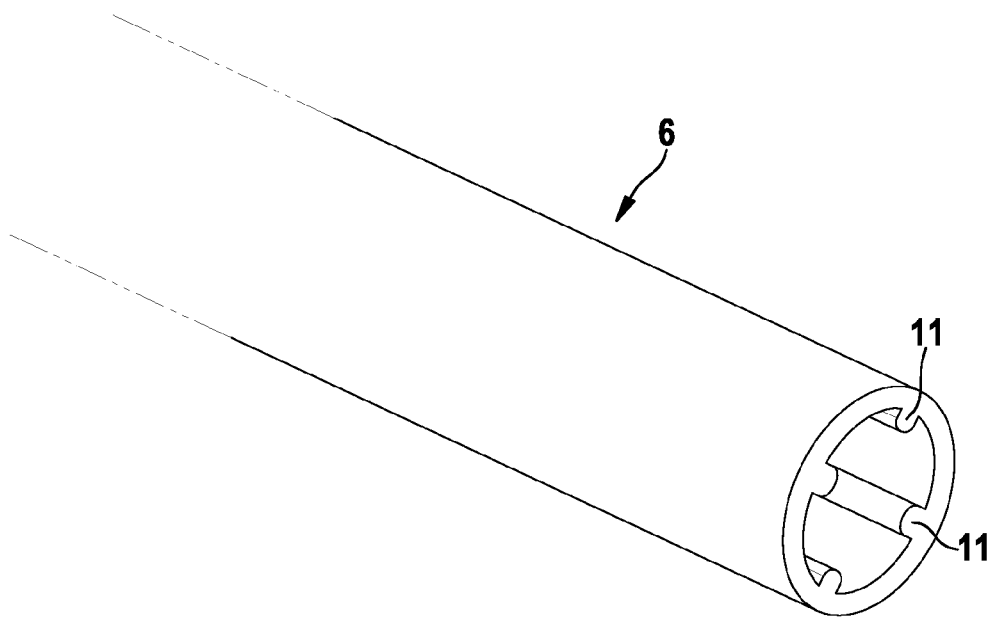
FIG. 6 shows an embodiment of a structuring of the inner surface of the sealing material, according to the disclosure.

As an alternative, or in addition to, the structuring of the electrode surface, the advancement of electrolyte, which is necessary for anodization to take place, can take place by way of an appropriate design of the sealing material. FIG. 6 shows an embodiment in which tubular sealing material 6, the inner surface of which has linear raised areas 11, which can function as transport channels for electrolyte once the feedthrough conductor has been assembled. Entirely analogously to the above-described structuring of the electrode surface, groove-shaped recesses can likewise be provided (although they are not depicted), and other shapes (nubs, recesses, etc.) and different geometric configurations are also possible in this case, as will be appreciated by one of ordinary skill in the art. Such structures are easily manufactured using known embossing techniques even during the process of fabricating a tubular elastic material.

Figure 7:
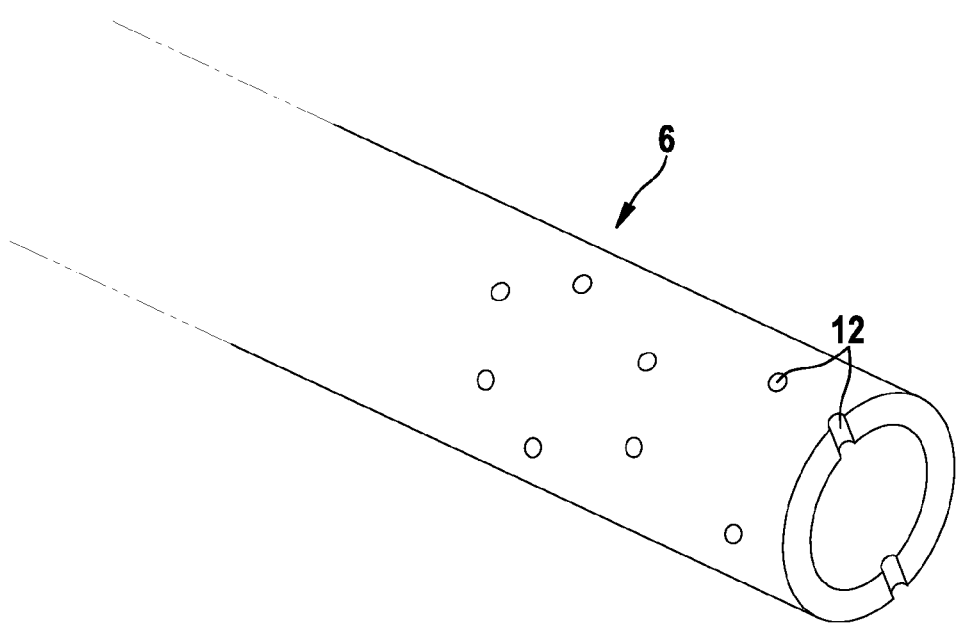
FIG. 7 shows an embodiment of a partial perforation of the sealing material, according to the disclosure.

FIG. 7 shows a further embodiment of sealing material 6 according to the disclosure. In this example, sealing material 6 comprises a distribution of pores 12 in the region in which electrode 2 should be reformed. Such openings can be created with the desired diameter and any surface density using known techniques (e.g., LASER drilling or punching) in the process of fabricating the tubular sealing material. The diameter of the pores is preferably in the range of micrometers to millimeters, however, other diameters are contemplated. The number of pores per surface element and the mean pore diameter are main variables that influence the quantity of electrolyte passing through.

To ensure that the anodizing of inner electrode section 2 remains limited to a predefined region, it is sufficient to limit the structuring of the electrode surface and/or the structuring or perforation of sealing material 6 to the desired region. For example, linear recesses 8 can be extended only up to ridge-shaped expansion 5 of electrode 2. Ridge 5, in combination with sealing material 6, which is pore-free and rests thereon entirely, therefore functions as a reliable seal and prevents electrolyte from advancing further.

All of the embodiments shown for advancing electrolyte to predefined regions of an electrode section can be combined in any manner possible. The quantity and distribution of the electrolyte can therefore be varied within a broad scope by way of the design of a feedthrough conductor, thereby making it possible to define conditions that are optimal for the forming process in terms of the properties of the electrode material.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A feedthrough contact for an electronic component comprising:
    a conductive electrode which is routed through an opening in a wall of the electronic component housing and is enclosed, at least in sections in the region of the opening, by an elastic sealing material which is impermeable to fluids and has insulating electrical properties, and wherein at least one section of the conductive electrode has a locally enlarged cross section, in the region of the passage through the opening, thereby compressing the elastic sealing material disposed between the electrode and the wall of the opening in this region such that the pressing of the sealing material against the electrode surface and the wall of the opening creates a seal that is impermeable to fluids,
wherein the section of the conductive electrode extending from the seal into the interior of the electronic component is designed as a capacitor contact and is enclosed in a tubular manner by the sealing material in this section, and wherein this section of the conductive electrode which is enclosed by the sealing material has a surface structure in the form of recesses or raised areas, or both, such that capillaries remain between the sealing material and the electrode surface, by way of which fluids can diffuse to the electrode surface.

2. The feedthrough contact according to claim 1, wherein the locally enlarged cross section is in the form of a ridge-shaped round profile.

3. The feedthrough contact according to claim 1, wherein the electronic component comprises a capacitor and the fluid comprises an electrolyte.

4. The feedthrough contact according to claim 1, wherein the electronic component comprises a capacitor for electrical implants.

5. The feedthrough contact according to claim 1, wherein the opening in the wall of the electronic component housing has a locally enlarged cross section, the profile of which is identical or similar to that of the locally enlarged cross section of the conductive electrode.

6. The feedthrough contact according to claim 5, wherein the locally enlarged cross section of the housing is in the region of the passage and wherein the section of the conductive electrode having the enlarged cross section is inserted together with the surrounding, compressed sealing material, into this region of the opening in a form-fit manner.

7. The feedthrough conductor according to claim 1, wherein the body-side opening and conductive electrode emerging there from are sealed using adhesive material.

8. The feedthrough conductor according to claim 7, wherein the adhesive material comprises epoxide resin.

9. The feedthrough conductor according to claim 1, wherein the recesses or raised areas, or both, are formed on the surface of the electrode section as lines.

10. The feedthrough conductor according to claim 9, wherein the recesses or raised areas, or both, are formed on the surface of the electrode section as straight lines or spiral shaped lines.

11. The feedthrough conductor according to claim 1, wherein the section of the conductive electrode extending from the seal into the interior of the electronic component is comprised of aluminum or an aluminum alloy.

12. The feedthrough conductor according to claim 1, wherein the section of the conductive electrode extending from the seal into the interior of the electronic component comprises an oxide layer formed on the surface by a forming process with the electrolyte.

13. The feedthrough conductor according to claim 1, wherein the section of the conductive electrode extending from the seal into the interior of the electronic component is comprised of a different metal or a different metal alloy than the electrode section extending from the seal toward the body side.

14. An electrical implant containing an electronic component having a feedthrough contact according to claim 1.

15. A feedthrough contact for an electronic component comprising:
a conductive electrode which is routed through an opening in a wall of the electronic component housing and is enclosed, at least in sections in the region of the opening, by an elastic sealing material which is impermeable to fluids and has insulating electrical properties, and wherein at least one section of the conductive electrode has a locally enlarged cross section, in the region of the passage through the opening, thereby compressing the elastic sealing material disposed between the electrode and the wall of the opening in this region such that the pressing of the sealing material against the electrode surface and the wall of the opening creates a seal that is impermeable to fluids,
wherein the section of the conductive electrode extending from the seal into the interior of the electronic component is designed as a capacitor contact and is enclosed in a tubular manner by the sealing material in this section, and wherein the sealing material has a surface structure in the form of recesses or raised areas, or both, only in the enclosing region of the sealing material facing the electrode side such that capillaries remain between the sealing material and the electrode surface, by way of which fluids can diffuse to the electrode surface.

16. The feedthrough conductor according to claim 15, wherein the recesses or raised areas, or both, are formed on the surface of the tubular sealing material as lines.

17. The feedthrough conductor according to claim 16, wherein the recesses or raised areas, or both, are formed on the surface of the tubular sealing material as straight lines or spiral shaped lines.

18. A feedthrough contact for an electronic component comprising:
a conductive electrode which is routed through an opening in a wall of the electronic component housing and is enclosed, at least in sections in the region of the opening, by an elastic sealing material which is impermeable to fluids and has insulating electrical properties, and wherein at least one section of the conductive electrode has a locally enlarged cross section, in the region of the passage through the opening, thereby compressing the elastic sealing material disposed between the electrode and the wall of the opening in this region such that the pressing of the sealing material against the electrode surface and the wall of the opening creates a seal that is impermeable to fluids,
wherein the section of the conductive electrode extending from the seal into the interior of the electronic component is designed as a capacitor contact and is enclosed in a tubular manner by the sealing material, and wherein the sealing material has a distribution of pores only in the enclosing region of the sealing material, by way of which the fluids can diffuse to the electrode surface.

* * * * *